US00PP24782P3

(12) United States Plant Patent
Harris

(10) Patent No.: US PP24,782 P3
(45) Date of Patent: Aug. 19, 2014

(54) AZALEA PLANT NAMED 'MNIHAR020'

(50) Latin Name: ***Rhododendron* sp.**
Varietal Denomination: MNIHAR020

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 74 days.

(21) Appl. No.: 13/506,311

(22) Filed: Apr. 11, 2012

(65) Prior Publication Data

US 2013/0276187 P1 Oct. 17, 2013

(51) Int. Cl.
*A01H 5/00* (2006.01)

(52) U.S. Cl.
USPC ..... Plt./240

(58) Field of Classification Search
CPC ..... A01H 5/02
USPC ..... Plt./240
See application file for complete search history.

(56) References Cited

U.S. PATENT DOCUMENTS

PP16,248 P2 * 2/2006 Lee ..... Plt./240

* cited by examiner

*Primary Examiner* — June Hwu
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, semi-double red flowers, easily propagated by semi-hardwood cuttings in late spring through summer, moderate growth rate under normal fertilization and moisture conditions; compact, broadly globose and freely branching in habit, grows well in containers, thrives in shade or sun and is hardy in Zone 7, is disclosed.

2 Drawing Sheets

Genus and species: *Rhododendron* sp.
Variety denomination: 'MNIHAR020'.

BACKGROUND OF THE NEW PLANT

The present invention is a new and distinct variety of evergreen azalea of the genus *Rhododendron*. This new azalea, hereinafter referred to as 'MNIHAR020', originated from a planned cross hybridization in 2000 between the female azalea plant 'Maria Derby' (unpatented) and the male azalea plant 'Conleb' (U.S. Plant Pat. No. 10,581) in a controlled environment in Lawrenceville, Ga. The present invention has a blooming period of mid March until mid April and late August until frost. 'MNIHAR020' has a compact, broadly globose, freely branching growth habit, and cold hardiness.

The new plant was first propagated via semi-hardwood cuttings in 2004 in Dearing, Ga. and has been asexually reproduced repeatedly by semi-hardwood cuttings in Dearing, Ga. for over 5 years and four generations. 'MNIHAR020' has been found to retain its distinctive characteristics through successive asexual propagations via semi-hardwood cuttings.

Plant Breeder's Rights for this variety have not been applied for. 'MNIHAR020' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red colored flowers;
3. Numerous semi-double flowers;
4. Easily propagated by semi-hardwood cuttings in late spring through summer;
5. Moderate growth rate under normal fertilization and moisture conditions;
6. Compact, broadly globose, freely branching growth habit;
7. Grows well in containers;
8. Thrives in shade or sun; and
9. Hardy in Zone 7.

DESCRIPTION OF THE PHOTOGRAPHS

This new azalea hybrid variety is illustrated by the accompanying photographs. The colors shown are as true as can be reasonably obtained by conventional photographic means. The photographs are of four-year-old plants grown in filtered shade and full sun in 2010 and 2011 in Dearing, Ga.

DETAILED BOTANICAL DESCRIPTION OF THE NEW PLANT

Figure 1:
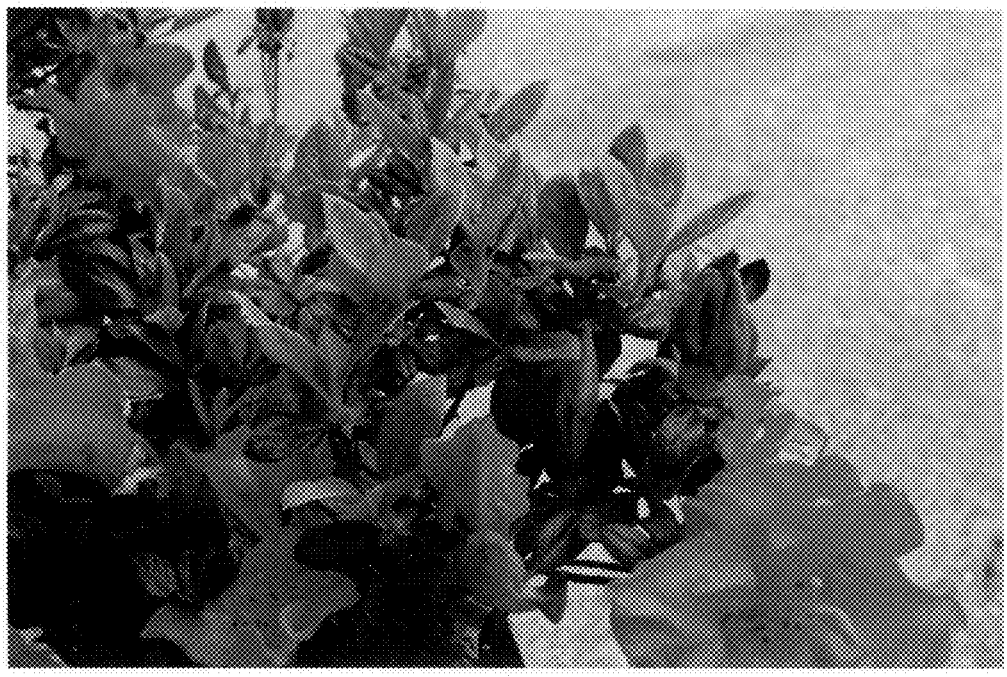
FIG. 1 is a close-up showing mature and immature foliage.
Figure 2:
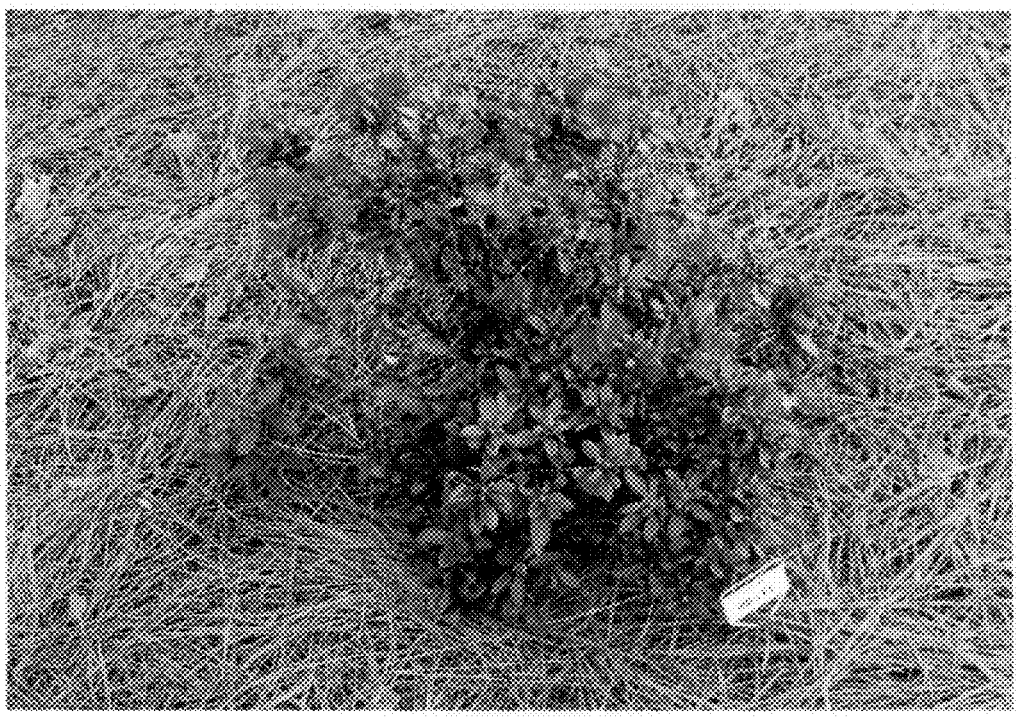
FIG. 2 shows mature foliage and growth habit and fall flowering of a four year old plant.
Figure 3:
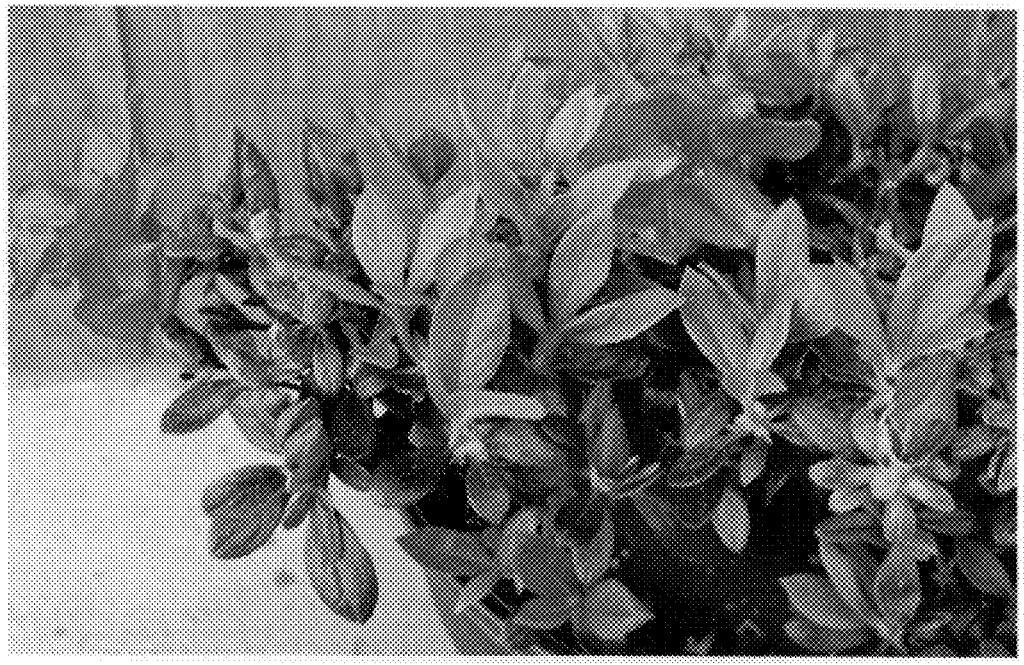
FIG. 3 is a close-up showing flower buds and new growth.
Figure 4:
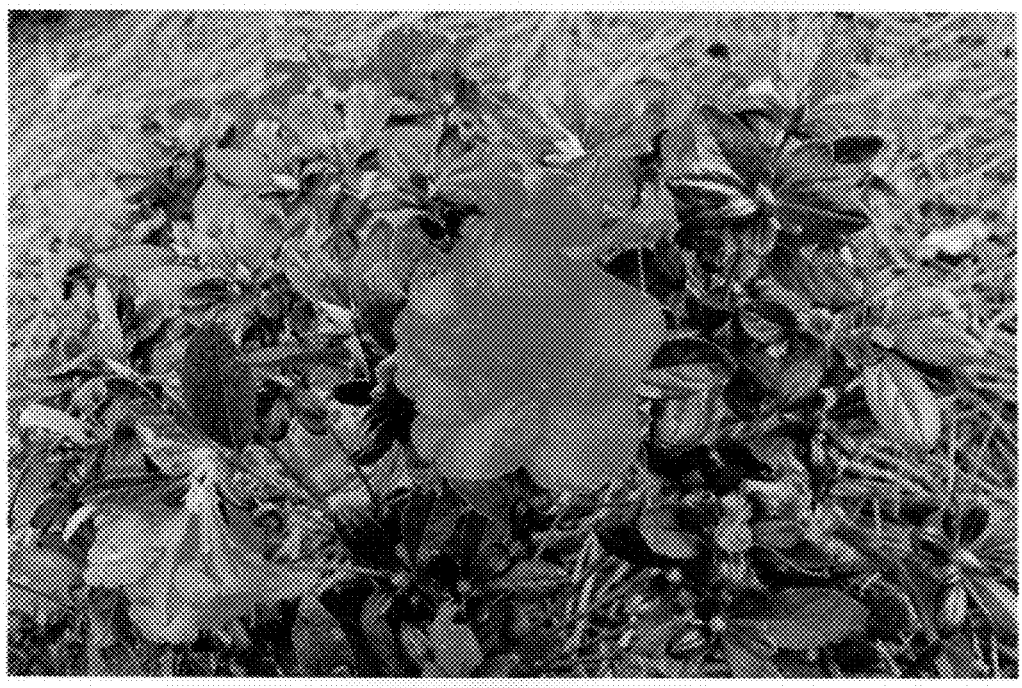
FIG. 4 is a close-up showing flower size, form, and color.

The following is a detailed description of the new variety of azalea based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, and 2011. The colors of the various plant parts are detailed with reference to The Royal Horticultural Society Colour Chart (2001).

Classification:

*Family*.—Ericaceae.

*Species*.—*Rhododendron* sp.

*Common name*.—Azalea.

*Denomination*.—'MNIHAR020'.

Parentage:

*Female parent*.—The azalea plant 'Maria Derby' (unpatented).

*Male parent*.—The azalea plant 'Conleb' (U.S. Plant Pat. No. 10,581).

Plant:

*Form*.—Compact, broadly globose.

*Texture*.—Medium.

*Height*.—76.2 cm to 91.44 cm.

*Width*.—121.92 cm to 152.4 cm.

*Growth habit*.—Freely branching; compact broadly globose in nature.

*Growth rate*.—Moderate growth rate under normal fertilization and moisture conditions. In a period of 5 years from a rooted cutting the plant reaches a height of 63.5 cm and a spread of 111.76 cm. The growth rate is normally averages about 13 cm per year; the plant reaches a height of 76.2 cm to 91.44 cm at maturity while maintaining a compact broadly globose habit due to the abundant deliquescent branch development. Spring growth: The date of initial spring growth is March 18, followed by continuous growth through fall.

*Life cycle*.—Perennial and evergreen.

Leaves:

*Arrangement*.—Alternate, simple, pubescent, and evergreen.

*Shape*.—Obelliptical to oblanceolate.

*Apex*.—Mucronate.

*Base*.—Attenuate.

*Margin*.—Entire.

*Length*.—3.6 cm.

*Width*.—1.6 cm.

*Venation pattern*.—Pinnate; the mid-veins and laterals are impressed on the upper surface and the prominent on the lower surface.

*Immature leaf*.—Upper surface: Color: Matte, RHS 144A (yellow-green). Pubescence: Strigose. Pubescence color: RHS N155A (white) and RHS 159A (orange-white). Lower surface: Color: Matte, RHS 144B (yellow-green). Pubescence: Strigose. Pubescence color: RHS N155A (white).

*Mature leaf*.—Upper surface: Color: Semi-glossy, RHS 139A (green). Pubescence: Strigose. Color: Mostly RHS N155A (white) with some RHS 159A (orange-white). Lower surface: Color: Matte, RHS 146B (yellow-green). Pubescence: Strigose. Pubescence color: RHS 165B (greyed-orange).

*Petiole*.—Length: 0.5 cm. Diameter: 0.2 cm by 0.15 cm. Pubescence: Strigose to villous. Length: 0.1 cm. Color: Immature: RHS N155A (white) and RHS 159A (orange-white). Mature: RHS 164A (greyed-orange). Color: Immature: RHS 145B (yellow-green). Mature: RHS 145C (yellow-green).

Stems:

*Form*.—Branched at terminal buds with some from axillary buds at leaf nodes.

*Young stems* (*actively growing, less than one year old*).—Color: RHS 144A (yellow-green). Pubescence: Strigose and villous. Pubescence color: Begins RHS N155A (white) maturing to RHS 164A (greyed-orange). Length of fully elongated flush: 4.4 cm on average. Diameter: 0.2 cm.

*Mature stems* (*one year old and older*).—Color: RHS N200C (grey-brown) and RHS N199B (grey-brown). Pubescence: Strigose, the quantity decreases with age of the stem. Pubescence color: RHS 167A (greyed-orange) in color. Length: 6.1 cm on average for full year's growth. Diameter: 0.3 cm in second year. Pith: Solid and uniform. Internode length: Average 1.0 cm on actively growing vegetative stems.

Flower buds:

*Arrangement and form*.—At terminal; borne in groups of one or two rarely three, sheathed by one to three modified leaf bracts. Bract length: Average 1.5 cm. Bract Width: 0.6 cm. Bract Color: RHS 144B (yellow-green) and RHS 145C (yellow-green).

*Shape*.—Ovate.

*Apex*.—Acute.

*Base*.—Rounded.

*Length* (*at tight bud*).—1.3 cm.

*Diameter* (*at tight bud*).—0.6 cm.

*Color* (*of scales*).—Immature: RHS 149D (yellow-green). Mature: RHS 149D (yellow-green) and RHS 144C (yellow-green).

*Texture*.—Matte; strigillose pubescence mainly at the apex.

*Pubescence color*.—RHS 166B (greyed-orange).

*Pedicel*.—Length: 0.6 cm at point bud begins to open. Diameter: 0.2 cm. Texture: Pubescent, sericeous pubescence. Pubescence color: RHS N155D (white). Color: RHS 145A (yellow-green) with slight RHS 46A (red) areas near the base of the calyx.

Calyx:

*Sepal length*.—0.6 cm.

*Sepal diameter*.—0.3 cm.

*Calyx diameter*.—0.5 cm from sepal apex to sepal apex.

*Sepal quantity*.—5.

*Texture*.—Pubescent, sericeous pubescence. Pubescence color: RHS 155D (white).

*Color*.—RHS 144B (yellow-green).

Flowers:

*Type*.—Perfect, semi-double flowers.

*Shape*.—Open funnel-shaped.

*Flowering habit and period*.—Borne on the current season's growth; four weeks beginning in mid March in Dearing, Ga.; flowering resumes late August and continues until frost which can be as late as November or December. Lastingness of flowers on the plant 4 to 6 days in the sun; 4 to 7 days in the shade.

*Fragrance*.—Absent.

*Diameter*.—6.8 cm.

*Depth*.—3.6 cm.

*Petals*.—Quantity per flower and arrangement: Five imbricate petals that are fused at the base and remain fused up to 2.2 cm from the base with 1 to 4 petaloids present. Shape: Obovate. Apex: Rounded. Base: Fused. Margin: Entire, slightly undulate and crisped. Texture (both upper and lower surfaces): Glabrous.

Length (of petals without spots): 4.5 cm. Width (of petals without spots): 3.0 cm. Length (of petals with spots): 4.3 cm. Width (of petals with spots): 2.7 cm. Color: Upper surface: RHS N34C (orange-red) the upper surface of the spots are RHS 46B (red). Lower surface: RHS N34C (orange-red), lower surface of spots are not visible.

Reproductive parts:

*Pistil*.—Quantity and form: Single, non-petaloid. Length: 4.1 cm. Diameter: 0.075 cm.

*Stigma*.—Color: RHS 175B (greyed-orange). Diameter: 0.15 cm.

*Style color*.—RHS 47D (red).

*Ovary*.—Strigose pubescence RHS N155A (white) with 5 locules.

*Ovary color*.—RHS 141A (green).

*Stamens*.—Quantity: 5 or 6 non-petaloids and 1 to 4 petaloids per flower. Length: Average 2.9 cm. Width: Average 1.4 cm for petaloid stamens. Color: RHS 46A (red).

*Anther*.—Length: 0.2 cm. Width: 0.1 cm. Color: RHS 200A (brown) and RHS 46A (red). Pollen: Abundant. Color: RHS 2D (yellow).

Fruit and seed: Observed.

*Maturity*.—The capsule matures in about 6 months in Dearing, Ga. and the fruit set is moderate and contains about 100 to 200 non-winged seeds.

*Capsule length*.—1.0 cm.

*Capsule width*.—0.8 cm.

*Capsule color*.—RHS 146A (yellow-green).

CULTURE

'MNIHAR020' grows well in a wide range of conditions and tolerates sun to shade. 'MNIHAR020' prefers moist, well-drained soil that is rich in organic matter and responds well to mulching and medium applications of fertilizer. 'MNIHAR020' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR020' is compared to parental varieties 'Maria Derby' (unpatented) and 'Conleb' (U.S. Plant Pat. No. 10,581).

TABLE 1

| Characteristic | 'MNIHAR020' | 'Maria Derby' | 'Conleb' U.S. Plant Pat. No. 10,581 |
|---|---|---|---|
| Plant Height (Mature) | 76.2 cm to 91.44 cm | 91.44 cm to 121.92 cm | 121.92 cm to 152.4 cm |
| Flower Diameter | 6.8 cm | 6.35 cm | 6.5 cm |
| Flower Form | Semi-double | Double to hose-in-hose | Single to semi-double |
| Flower Color | Red | Deep reddish orange | Red |
| Bloom Period | Mid March to mid April and late August until frost | May | April and late July until frost |
| Hardy Zone | 7 | 6b | 7 |
| Stamen Number | 5 to 6 | 0 to 5 | 0 to 9 |
| Stamen Type | Petaloid and non-petaloid | Petaloid and non-petaloid | Petaloid and non-petaloid |

When 'MNIHAR020' is compared to the commercial variety 'Roblen' (U.S. Plant Pat. No. 16,248), 'MNIHAR020' has a compact broadly globose growth habit with a height of 63.5 cm and a spread of 111.76 cm in 5 years, while 'Roblen' has a height of 91.44 cm and a spread of 60.96 cm in six years. Additionally, 'MNIHAR020' produces semi-double flowers, while 'Roblen' has single to semi-double flowers.

I claim:

1. A new variety of azalea plant named 'MNIHAR020' as herein shown and described.

* * * * *